(12) United States Patent
Keller et al.

(10) Patent No.: US 11,245,860 B2
(45) Date of Patent: Feb. 8, 2022

(54) REDUCTION OF IMAGE LAG IN AN X-RAY DETECTOR PANEL

(71) Applicant: Varian Medical Systems International AG, Palo Alto, CA (US)

(72) Inventors: Simon Keller, Brugg (CH); Daniel Morf, Buch am Irchel (CH)

(73) Assignee: VARIAN MEDICAL SYSTEMS INTERNATIONAL AG

( * ) Notice: Subject to any disclaimer, the term of this patent is extended or adjusted under 35 U.S.C. 154(b) by 106 days.

(21) Appl. No.: 16/714,501

(22) Filed: Dec. 13, 2019

(65) Prior Publication Data

US 2021/0185245 A1 Jun. 17, 2021

(51) Int. Cl.
H04N 5/32 (2006.01)
A61B 6/00 (2006.01)
G01T 1/24 (2006.01)
H04N 5/374 (2011.01)

(52) U.S. Cl.
CPC ............ *H04N 5/32* (2013.01); *A61B 6/4233* (2013.01); *G01T 1/247* (2013.01); *H04N 5/3741* (2013.01); *H04N 5/3742* (2013.01)

(58) Field of Classification Search
CPC .. A61B 6/4233; H04N 5/3741; H04N 5/3742; H04N 5/32; G01T 1/247
See application file for complete search history.

(56) References Cited

U.S. PATENT DOCUMENTS

| | | | |
|---|---|---|---|
| 2004/0068169 A1* | 4/2004 | Mansfield | A61B 6/4452 600/407 |
| 2007/0081628 A1* | 4/2007 | Dasani | G01N 23/04 378/62 |
| 2015/0070554 A1* | 3/2015 | Shimizu | H04N 5/3765 348/308 |
| 2016/0084969 A1* | 3/2016 | Sato | H04N 5/361 250/370.08 |
| 2018/0091754 A1* | 3/2018 | Okura | H04N 5/3745 |

\* cited by examiner

*Primary Examiner* — Michael C Bryant
(74) *Attorney, Agent, or Firm* — Su IP Consulting

(57) ABSTRACT

A radiation therapy system is configured with fast readout of X-ray images with significantly reduced image lag. A reset phase is included in the process of acquiring an X-ray image to reduce image lag in a subsequently acquired X-ray image. During the reset phase, residual charge is concurrently transferred from multiple arrays of pixel detector elements in an X-ray detector panel. As a result, image lag present in a subsequent X-ray image is minimized or otherwise reduced.

20 Claims, 14 Drawing Sheets

REDUCTION OF IMAGE LAG IN AN X-RAY DETECTOR PANEL

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on the planning target volume that spares the surrounding normal tissue from receiving doses above specified tolerances, thereby minimizing risk of damage to healthy tissue. Prior to the delivery of radiation therapy, an imaging system is typically employed to provide a three dimensional image of the target tissue and surrounding area. From such imaging, the size and mass of the target tissue can be estimated and an appropriate treatment plan generated and planning target volume determined.

So that the prescribed dose is correctly supplied to the planning target volume (i.e., the target tissue) during radiation therapy, the patient should be correctly positioned relative to the linear accelerator that provides the radiation therapy. Typically, dosimetric and geometric data are checked before and during the treatment, to ensure correct patient placement and that the administered radiotherapy treatment matches the previously planned treatment. This process is referred to as image guided radiation therapy (IGRT), and involves the use of an imaging system to view target tissues during or prior to radiation treatment delivery to the planning target volume. IGRT incorporates imaging coordinates from the treatment plan to ensure the patient is properly aligned for treatment in the radiation therapy device.

SUMMARY

In accordance with at least some embodiments of the present disclosure, a radiation therapy system is configured with fast readout of X-ray images without significantly increasing image lag. In the embodiments, a reset phase is included in the process of acquiring an X-ray image to reduce image lag in a subsequently acquired X-ray image. Specifically, during the reset phase, residual charge is concurrently transferred from multiple arrays of pixel detector elements in an X-ray detector panel. As a result, image lag present in a subsequent X-ray image is minimized or otherwise reduced.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
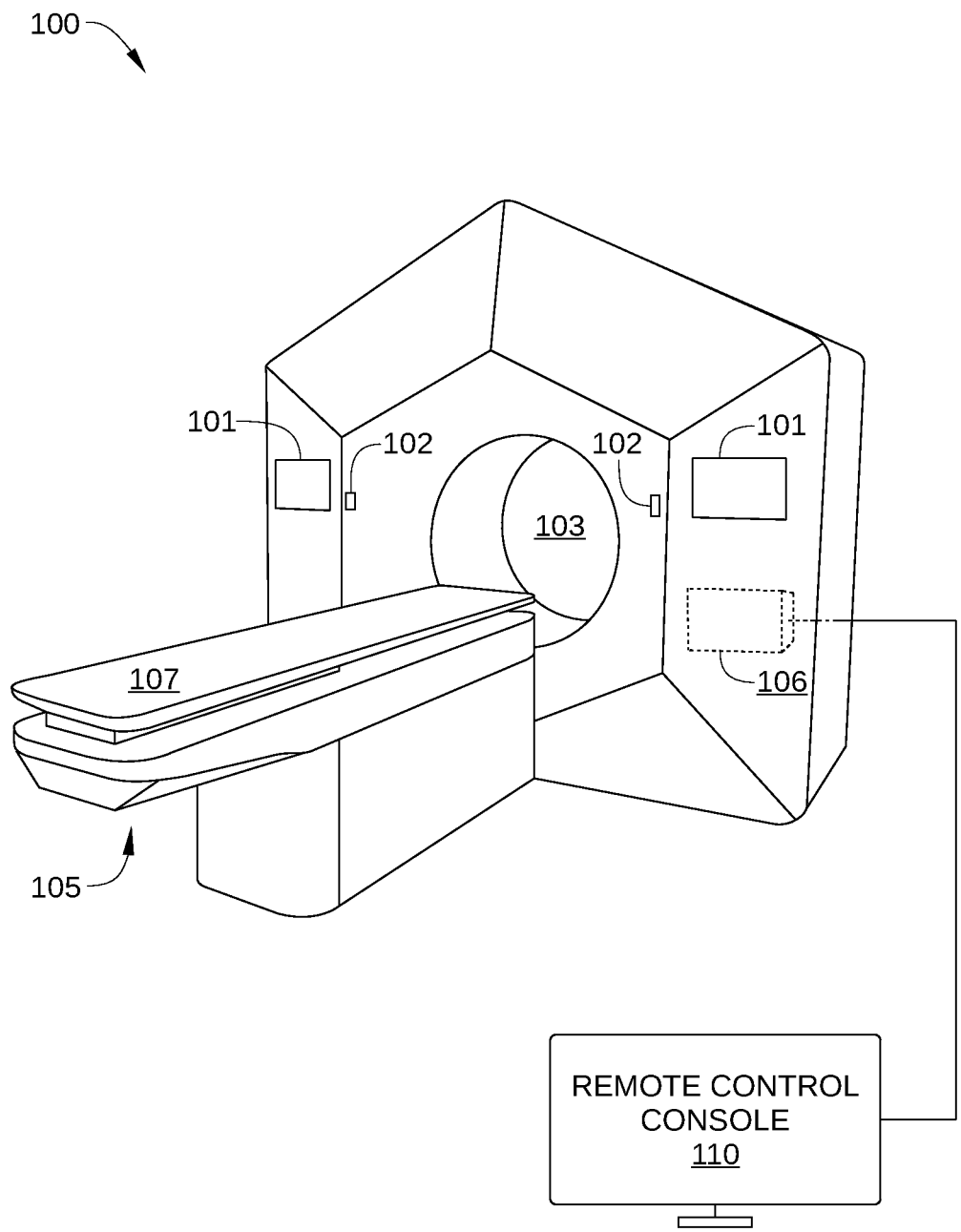
FIG. 1 is a perspective view of a radiation therapy system that can beneficially implement various aspects of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

INTRODUCTION

Image guided radiation therapy (IGRT) is used to treat tumors in areas of the body that are subject to voluntary movement, such as the lungs, or involuntary movement, such as organs affected by peristalsis. IGRT involves the use of an imaging system to view target tissues (also referred to as the "target volume") while radiation treatment is delivered thereto. In IGRT, image-based coordinates of the target volume from a previously determined treatment plan are compared to image-based coordinates of the target volume determined during the application of the treatment beam. In this way, changes in the surrounding organs at risk and/or motion or deformation of the target volume relative to the radiation therapy system can be detected. Consequently, dose limits to organs at risk are accurately enforced based on the daily position and shape, and the patient's position and/or the treatment beam can be adjusted to more precisely target the radiation dose to the tumor. For example, in pancreatic tumor treatments, organs at risk include the duodenum and stomach. The shape and relative position of these organs at risk with respect to the target volume can vary significantly from day-to-day. Thus, accurate adaption to the shape and relative position of such organs at risk enables dose sparing to those organs at risk and escalation of the dose to the target volume and better therapeutic results.

In some conventional IGRT radiation systems, motion of soft tissues is detected during application of the treatment beam via fiducial markers, such as gold seeds. However, the use of fiducial markers has numerous drawbacks, particularly the invasive surgical procedures required for placement of the markers. Specifically, the laproscopic insertion of fiducial markers requires additional time and clinical resources, such as an operating room, anesthesia, antibiotics, and the participation of numerous additional medical specialists.

Alternatively, in some conventional IGRT radiation systems, motion of soft tissues is detected during application of the treatment beam via magnetic resonance imaging (MRI). However, MRI-based IGRT also has drawbacks. First, MRI-based IGRT systems are generally larger, more complex, and more expensive than radiation therapy systems that employ X-ray imaging. Second, detecting motion or deformation of the target volume via MRI generally involves monitoring images associated with a 2D slice that passes through the target volume. As a result, target volume motion or deformation that occurs anywhere outside of (or perpendicular to) the 2D slice being monitored is difficult to detect, which can significantly impact the accuracy of the radiation dose being applied.

Alternatively, in some conventional IGRT radiation systems, motion of soft tissues is detected during application of treatment X-rays via imaging X-rays that are also directed through the target volume. For example, volumetric image data for the target volume can be reconstructed based on X-ray projection images of the target volume that are generated with a computed tomography (CT) or cone-beam CT (CBCT) process. In a CT or CBCT process, a plurality of X-ray projection images are generated by the imaging X-rays passing though the target volume and onto an X-ray detector panel or other X-ray imaging device. Generally, in IGRT applications, faster CT or CBCT acquisition is beneficial, since faster acquisition of target volume images enables faster detection of motion or deformation of the target volume and/or changes in the surrounding organs at risk.

The speed of CT or CBCT acquisition is strongly dependent on panel readout time of the X-ray detector panel generating the X-ray projection images of the target volume and surrounding organs at risk. Because all pixels in one row of an X-ray detector panel are typically read out simultaneously, the minimum panel readout time is approximately equal to the pixel readout time multiplied by the number of rows in the X-ray detector panel. Thus, application of a shorter pixel readout time in an X-ray detector panel can significantly reduce panel readout time. However, a shorter pixel readout time in certain X-ray detector panels, such as amorphous silicon-based panels, necessarily causes greater image lag in X-ray images generated by such X-ray detector panels. Image lag is the carryover of charge associated with the pixels of one X-ray image to the pixels of a subsequent X-ray image, and can cause significant image artifacts. Consequently, in implementing faster X-ray image acquisition, there is a well-known trade-off between imaging framerate and image lag.

In light of the above, there is a need in the art for improved systems and techniques for increasing imaging framerate in a radiation therapy system without increasing image lag in the resultant X-ray images. One such embodiment is illustrated in FIG. 1.

System Overview

FIG. 1 is a perspective view of a radiation therapy system 100 that can beneficially implement various aspects of the present disclosure. Radiation therapy (RT) system 100 is a radiation system configured to detect intra-fraction motion in near-real time using X-ray imaging techniques. Thus, RT system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) that generates a megavolt (MV) treatment beam of high energy X-rays, a kilovolt (kV) X-ray source, an X-ray imager, and, in some embodiments, an MV electronic portal imaging device (EPID). By way of example, radiation therapy system 100 is described herein configured with a circular gantry. In other embodiments, radiation therapy system 100 can be configured with a C-gantry capable of infinite rotation via a slip ring connection, a ring gantry with a slip ring, a C-gantry with a wind-up configuration, and the like.

Generally, RT system 100 is capable of kV imaging of a target volume during application of an MV treatment beam, so that an IGRT process can be performed using X-ray imaging rather than MRI. RT system 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. RT system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as button and/or switches, that enable a user to operate base positioning assembly 105 to automatically and precisely position couch 107 to a predetermined location with respect to bore 103. Motion controls 102 also enable a user to manually position couch 107 to a predetermined location. In some embodiments, RT system 100 further includes one or more cameras (not shown) in the treatment room for patient monitoring.

Figure 2:
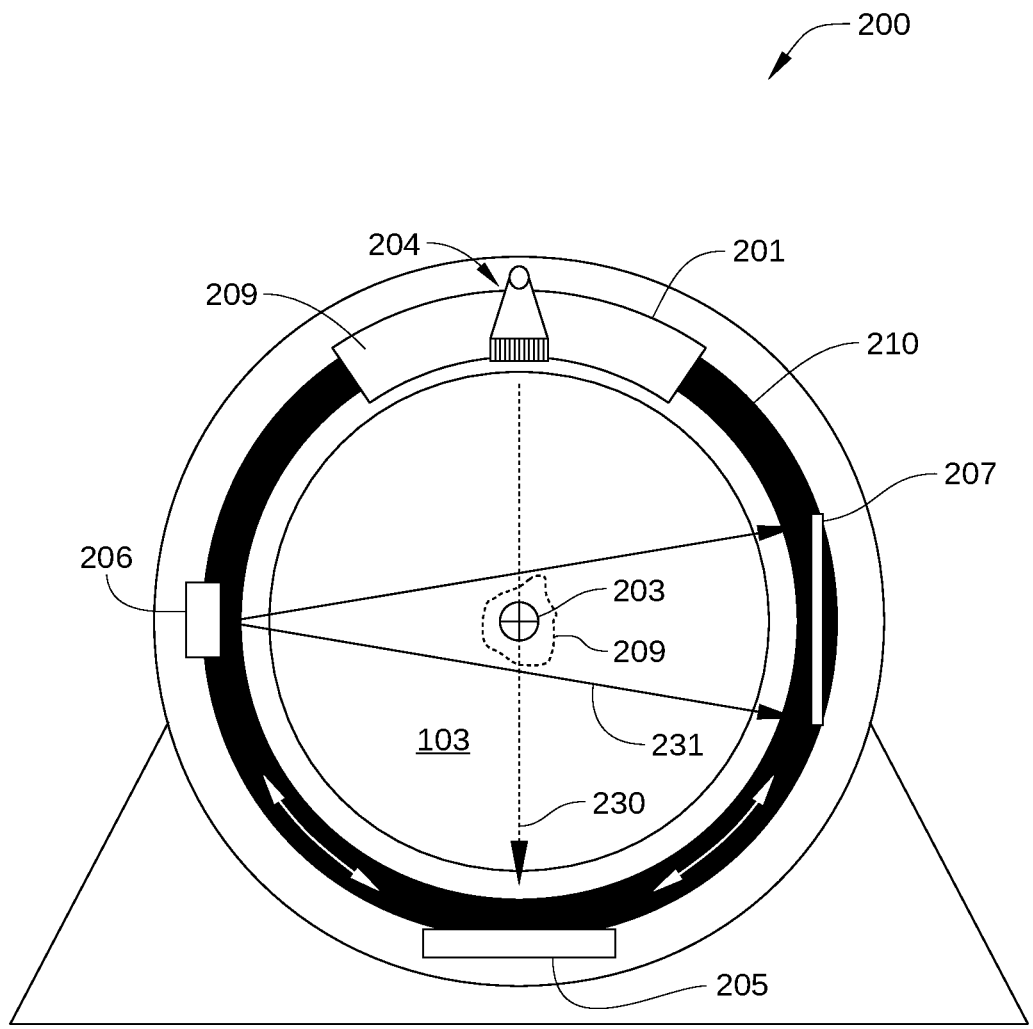
FIG. 2 schematically illustrates a drive stand and a gantry of the radiation system of FIG. 1, according to various embodiments of the current disclosure.

FIG. 2 schematically illustrates a drive stand 200 and gantry 210 of RT system 100, according to various embodiments of the current disclosure. Covers, base positioning assembly 105, couch 107, and other components of RT system 100 are omitted in FIG. 2 for clarity. Drive stand 200 is a fixed support structure for components of RT treatment system 110, including gantry 210 and a drive system 201 for rotatably moving gantry 210. Drive stand 200 rests on and/or is fixed to a support surface that is external to RT treatment system 110, such as a floor of an RT treatment facility. Gantry 210 is rotationally coupled to drive stand 200 and is a support structure on which various components of RT system 100 are mounted, including a linear accelerator (LINAC) 204, an MV electronic portal imaging device (EPID) 205, an imaging X-ray source 206, and an X-ray imager 207. During operation of RT treatment system 110, gantry 210 rotates about bore 103 when actuated by drive system 201.

Drive system 201 rotationally actuates gantry 210. In some embodiments, drive system 201 includes a linear motor that can be fixed to drive stand 200 and interacts with a magnetic track (not shown) mounted on gantry 210. In other embodiments, drive system 201 includes another suitable drive mechanism for precisely rotating gantry 210 about bore 201. LINAC 204 generates an MV treatment beam 230 of high energy X-rays (or in some embodiments electrons) and EPID 205 is configured to acquire X-ray images with treatment beam 230. Imaging X-ray source 206 is configured to direct a conical beam of X-rays, referred to herein as imaging X-rays 231, through an isocenter 203 of RT system 100 to X-ray imager 207, and isocenter 203 typically corresponds to the location of a target volume 209 to be treated. In the embodiment illustrated in FIG. 2, X-ray imager 207 is depicted as a planar device, whereas in other embodiments, X-ray imager 207 can have a curved configuration.

X-ray imager 207 receives imaging X-rays 231 and generates suitable projection images therefrom. According to certain embodiments, such projection images can then be employed to construct or update portions of imaging data for a digital volume that corresponds to a three-dimensional (3D) region that includes target volume 209. That is, a 3D image of such a 3D region is reconstructed from the projection images. In the embodiments, cone-beam computed tomography (CBCT) and/or digital tomosynthesis (DTS) can be used to process the projection images generated by X-ray imager 207. CBCT is typically employed to acquire projection images over a relatively long acquisition arc, for example over a rotation of 180° or more of gantry 210. As a result, a high-quality 3D reconstruction of the imaged volume can generated. CBCT is often employed at the beginning of a radiation therapy session to generate a set-up 3D reconstruction. For example, CBCT may be employed immediately prior to application of treatment beam 230 to generate a 3D reconstruction confirming that target volume 209 has not moved or changed shape.

In some embodiments, partial-data reconstruction may be performed by RT system 100 during portions of an IGRT process in which partial image data is employed to generate a 3D reconstruction of target volume 209. For example, as treatment beam 230 is directed to isocenter 203 while gantry 210 rotates through a treatment arc, DTS image acquisitions can be performed to generate image data for target volume 209. Because DTS image acquisition is performed over a relatively short acquisition arc, for example between about 10° and 60°, near real-time feedback for the shape and position of target volume 209 can be provided by DTS imaging during the IGRT process. Alternatively, CBCT may be employed during portions of an IGRT process to generate a 3D reconstruction of target volume 209. According to various embodiments described below, higher framerate X-ray images having little or no increased image lag can be generated for either scenario. Such higher framerate X-ray images are highly beneficial for generating accurate image data for target volume 209, either for CBCT or DTS image acquisition.

In some embodiments, X-ray imager 207 includes a glass plate with a matrix or array of pixel detector elements, or pixels, formed thereon that each convert incident X-ray photons to electrical charge. In embodiments in which X-ray imager 207 is configured as an indirect flat panel detector, a scintillator material in X-ray imager 207 is excited by incident X-rays and emits light, which is detected by a plurality of photodiodes. Each photodiode generates a signal (e.g., an accumulated voltage that is proportional to incident light intensity) for a different pixel of what will eventually become a digital image. An encoder included in X-ray imager 207 then interprets each of these voltages and assigns a value to each that is proportional to the voltage. One such embodiment of X-ray imager 207 is illustrated in FIG. 3.

Figure 3:
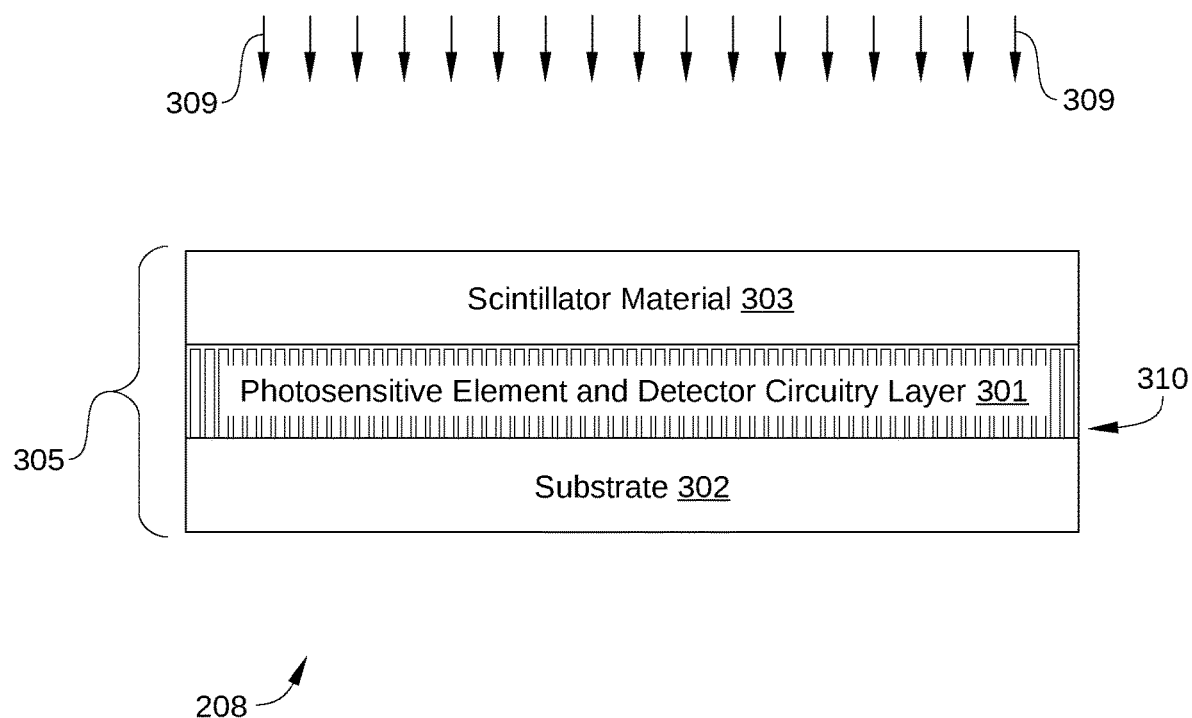
FIG. 3 schematically illustrates a cross-sectional view of an X-ray imager, according to one embodiment of the disclosure.

FIG. 3 schematically illustrates a cross-sectional view of X-ray imager 207, according to one embodiment of the disclosure. As shown, X-ray imager 207 includes a photosensitive element and detector circuitry layer 301 formed on a substrate 302. In addition, X-ray imager 207 includes a layer of scintillator material 303 formed on photosensitive element and detector circuitry layer 301. Also shown are incident X-rays 309 that have passed through a patient, sample, or other object of interest after being generated by imaging X-ray source 206 (shown in FIG. 2). Together, photosensitive element and detector circuitry layer 301, substrate 302, and scintillator material 303 form an X-ray imaging array 305. It is noted that photosensitive element and detector circuitry layer 301 is generally formed from a plurality of processing layers, and that X-ray imaging array 305 may include additional material layers not illustrated in FIG. 3.

Photosensitive element and detector circuitry layer 301 generally includes a plurality of pixel detector elements 310. Each pixel detector element 310 includes a photosensitive element, such as a photodiode, a photogate, or a phototransistor, as well as any other circuitry suitable for operation as a pixel detector element in X-ray imager 207. In some embodiments, the photosensitive elements of pixel detector element 310 are amorphous silicon-based semiconductor devices. Photosensitive element and detector circuitry layer 301 may also include thin-film transistors (TFTs) for reading out the digital signals from pixel detector elements 310. Scintillator material 303 may include one or more material layers including, but no limited to, gadolinium oxisulfide ($Gd_2O_2S$:Tb), cadmium tungstate ($CdWO_4$), bismuth germanate ($Bi_4Ge_3O_{12}$ or BGO), cesium iodide (CsI), or cesium iodide thallium (CsI:Tl)), among others.

In the embodiment illustrated in FIG. 3, X-ray imager 207 is depicted as an indirect flat panel detector, in which X-ray photons are converted to other light photons that are in turn detected and converted into charge. In other embodiments, X-ray imager 207 can be a direct flat panel detector (FPD). In a direct FPD, incident X-ray photons are converted directly into charge in an amorphous selenium layer, and the resultant charge pattern therein is read out by suitable hardware, such as a thin-film transistor (TFT) array, an active matrix array, microplasma line addressing, or the like.

In the embodiment illustrated in FIG. 2, RT system 100 includes a single X-ray imager and a single corresponding imaging X-ray source. In other embodiments, RT system 100 can include two or more X-ray imagers, each with a corresponding imaging X-ray source. Thus, in such embodiments, RT system 100 includes a first imaging X-ray source and a corresponding X-ray imager mounted on gantry 210 and a second imaging X-ray source and corresponding X-ray imager mounted on gantry 210. In such embodiments, the inclusion of multiple X-ray imagers in RT system 100 facilitates the generation of projection images (for reconstructing the target volume) over a shorter image acquisition arc. For instance, when RT system 100 includes two X-ray imagers and corresponding X-ray sources, an image acquisition arc for acquiring projection images of a certain image quality can be approximately half that for acquiring projection images of a similar image quality with a single X-ray imager and X-ray source. Further, in such embodiments, the inclusion of multiple X-ray imagers in RT system 100 facilitates the use of multiple X-ray source energies, since the first imaging X-ray source and the second imaging X-ray source can each operate at a different energy. Alternatively, in embodiments in which RT system 100 includes a single imaging X-ray source, the single imaging X-ray source can be configured as a multi-energy source.

The projection images generated by X-ray imager 207 are used to construct imaging data for a digital volume of patient anatomy within a 3D region that includes the target volume. Alternatively or additionally, such projection images can be used to update portions of existing imaging data for the digital volume corresponding to the 3D region. One embodiment of such a digital volume is described below in conjunction with FIG. 4.

Figure 4:
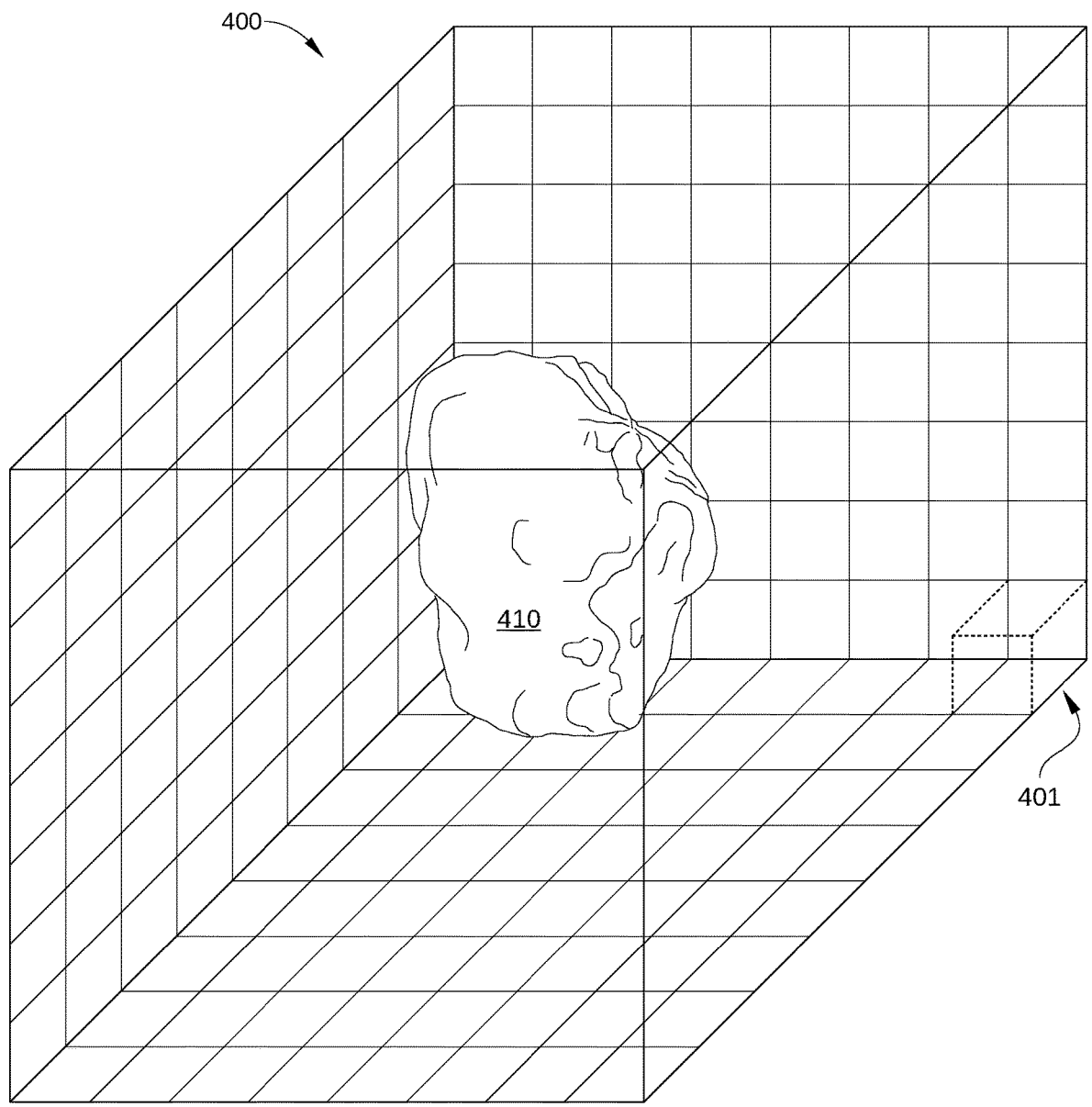
FIG. 4 schematically illustrates a digital volume that is constructed based on projection images generated by one or more X-ray imagers included in the RT system of FIG. 1, according to various embodiments of the current disclosure.

FIG. 4 schematically illustrates a digital volume 400 that is constructed based on projection images generated by one or more X-ray imagers included in RT system 100, according to various embodiments of the current disclosure. For example, in some embodiments, the projection images can be generated by a single X-ray imager, such as X-ray imager 207, and in other embodiments the projection images can be generated by multiple X-ray imagers.

Digital volume 400 includes a plurality of voxels 401 (dashed lines) of anatomical image data, where each voxel 401 corresponds to a different location within digital volume 400. For clarity, only a single voxel 401 is shown in FIG. 4. Digital volume 400 corresponds to a 3D region that includes target volume 410. In FIG. 4, digital volume 400 is depicted as an 8×8×8 voxel cube, but in practice, digital volume 400 generally includes many more voxels, for example orders of magnitude more than are shown in FIG. 4.

For purposes of discussion, target volume 410 can refer to the gross tumor volume (GTV), clinical target volume (CTV), or the planning target volume (PTV) for a particular treatment. The GTV depicts the position and extent of the gross tumor, for example what can be seen or imaged; the CTV includes the GTV and an additional margin for sub-clinical disease spread, which is generally not imageable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by embodiments of the disclosure.

According to various embodiments described below, image information associated with each voxel 401 of digital volume 400 is constructed from projection images generated by single or multiple X-ray imagers, for example via a CBCT or DTS process. In some embodiments, image information associated with some or all of voxels 401 of digital volume 400 is updated via projection images generated by the single or multiple X-ray imagers via a DTS process. For example, such a DTS process can be employed after a portion of a planned treatment has begun and before the planned treatment has completed. In this way, the location and shape of target volume 410 can be confirmed while the treatment is underway. Thus, if a sufficient portion of the target volume 410 is detected to extend outside a threshold region, the treatment can either be aborted or modified. In such an instance, modification of the treatment can be accomplished by adjusting patient position and/or the treatment beam.

Figure 5:
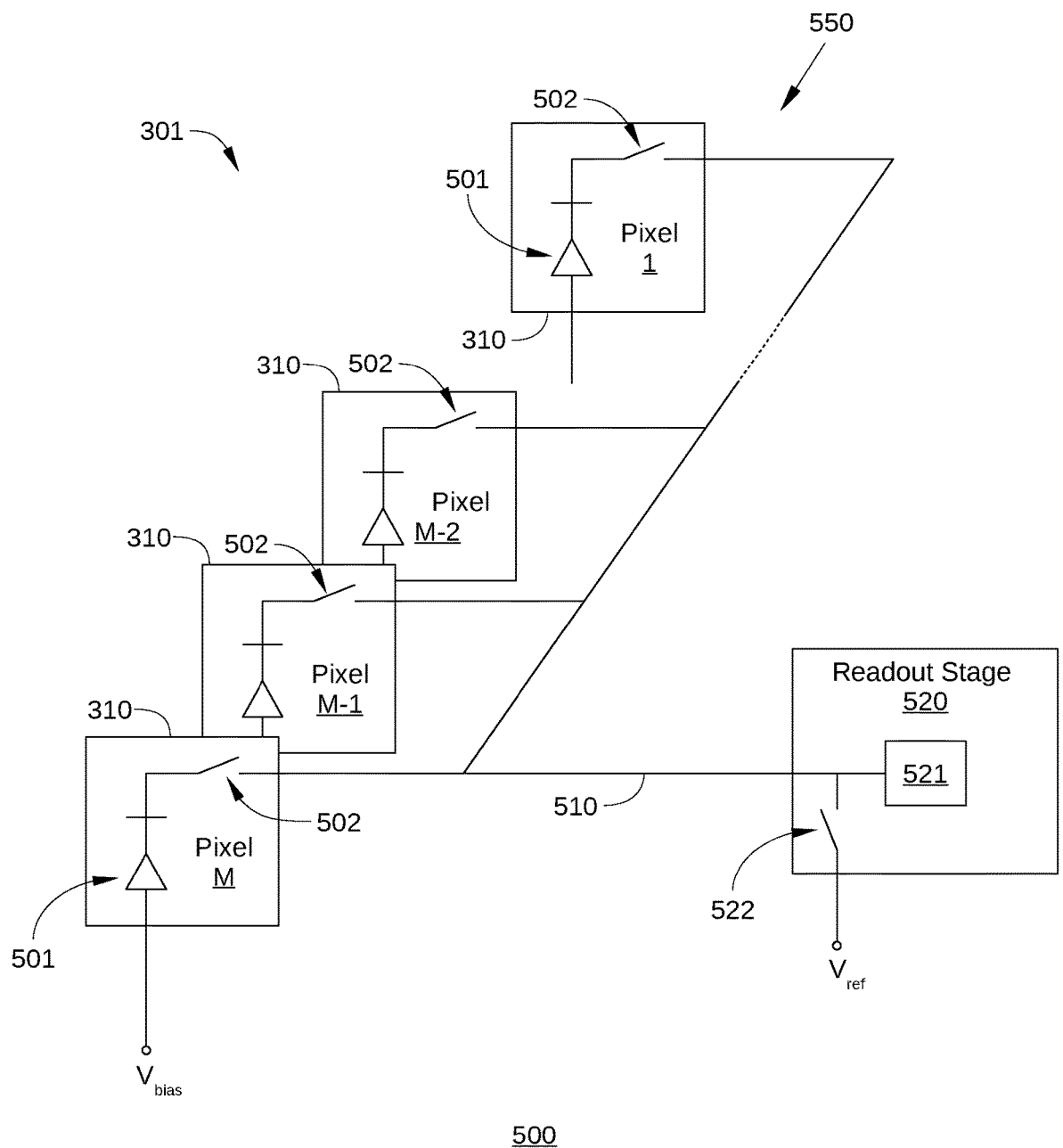
FIG. 5 is a partial circuit diagram of a photosensitive element and detector circuitry layer included in the X-ray imager of FIG. 3, according to one embodiment of the disclosure.

FIG. 5 is a partial circuit diagram 500 of photosensitive element and detector circuitry layer 301, according to one embodiment of the disclosure. Photosensitive element and detector circuitry layer 301 can be included in a suitable X-ray detector panel, such as X-ray imager 207 in FIG. 2. As shown, photosensitive element and detector circuitry layer 301 includes a plurality of pixel detector elements 310 that are each communicatively coupled to a readout stage 520 via a common data line 510. Generally, photosensitive element and detector circuitry layer 301 includes an M×N matrix of pixel detector elements 310, where M equals the number of rows of pixel detector elements 310 and N equals the number of columns of pixel detector elements 310. Generally, M and N have values on the order of about 1000 to 4000 in an X-ray detector panel. For clarity, only a single array of pixel detector elements 310 that forms one column of M pixel detector elements 310 is shown in FIG. 5. In practice, photosensitive element and detector circuitry layer 301 includes a total of N such arrays of pixel detector elements 310, where each array forms one of the M rows of pixels of an X-ray detector panel.

In the embodiment illustrated in FIG. 5, each pixel detector element 310 includes a photodiode 501 and a readout switch 502 that communicatively couples the photodiode 501 to readout stage 520. As shown, each photodiode 501 is communicatively coupled to a bias voltage $V_{bias}$ and is also communicatively coupled to data line 510 via a respective readout switch 502. Each readout switch 502 is typically formed as part of the associated pixel detector element 310. Alternatively, in some embodiments, each readout switch 502 is formed proximate to the associated pixel detector element 310. In either case, readout switches 502 are generally formed as part of photosensitive element and detector circuitry layer 301. For example, in some embodiments, readout switches 502 are implemented as thin-film transistors (TFTs) that are formed on the same substrate as the pixel detector elements 310.

Readout stage 520 is a readout device configured to readout accumulated charge from the pixel detector elements 310 of a particular column 550 of pixel detector elements 310. Readout stage 520 reads out a particular pixel detector element 310 (for example, the pixel detector element 310 associated with Pixel M-2) when the readout switch 502 for that particular pixel detector element 310 (for example, readout switch 502 associated with Pixel M-2)

closes and communicatively couples that pixel detector element 310 to data line 510. In operation, for each other column (not shown) of photosensitive element and detector circuitry layer 301, a single pixel detector element 310 can be simultaneously readout by the readout stage 520 associated with the column. Thus, a complete row of pixel detector elements 310 of photosensitive element and detector circuitry layer 301 can be read out at one time by the appropriately timed closing of one readout switch 502 in each column of pixel detector elements 310.

Readout stage 520 is configured to convert analog signals, such as charge accumulated in pixel detector elements 310, to digital X-ray image signals. In some embodiments, readout stage 520 includes conversion circuitry 521 for converting such signals to digital X-ray image signals. Conversion circuitry 521 can include any technically feasible circuitry suitable for performing such conversions. For example, in some embodiments, conversion circuitry 521 includes an analog-to-digital converter, an analog front-end, or the like. In addition, in the embodiment illustrated in FIG. 5, readout stage 520 includes a reset switch 522 that is configured to communicatively couple data line 510 to a reference voltage $V_{ref}$, such as ground or any other suitable reference voltage. Thus, when a readout switch 502 of a particular pixel detector element 310 is closed while reset switch 522 is closed, charge currently accumulated in that particular pixel detector element 310 discharges down to the reference voltage $V_{ref}$. By contrast, when a readout switch 502 of a particular pixel detector element 310 is closed while reset switch 522 is open, charge currently accumulated in that particular pixel detector element 310 discharges to the readout stage 520 and is read by conversion circuitry 521.

Figure 6:
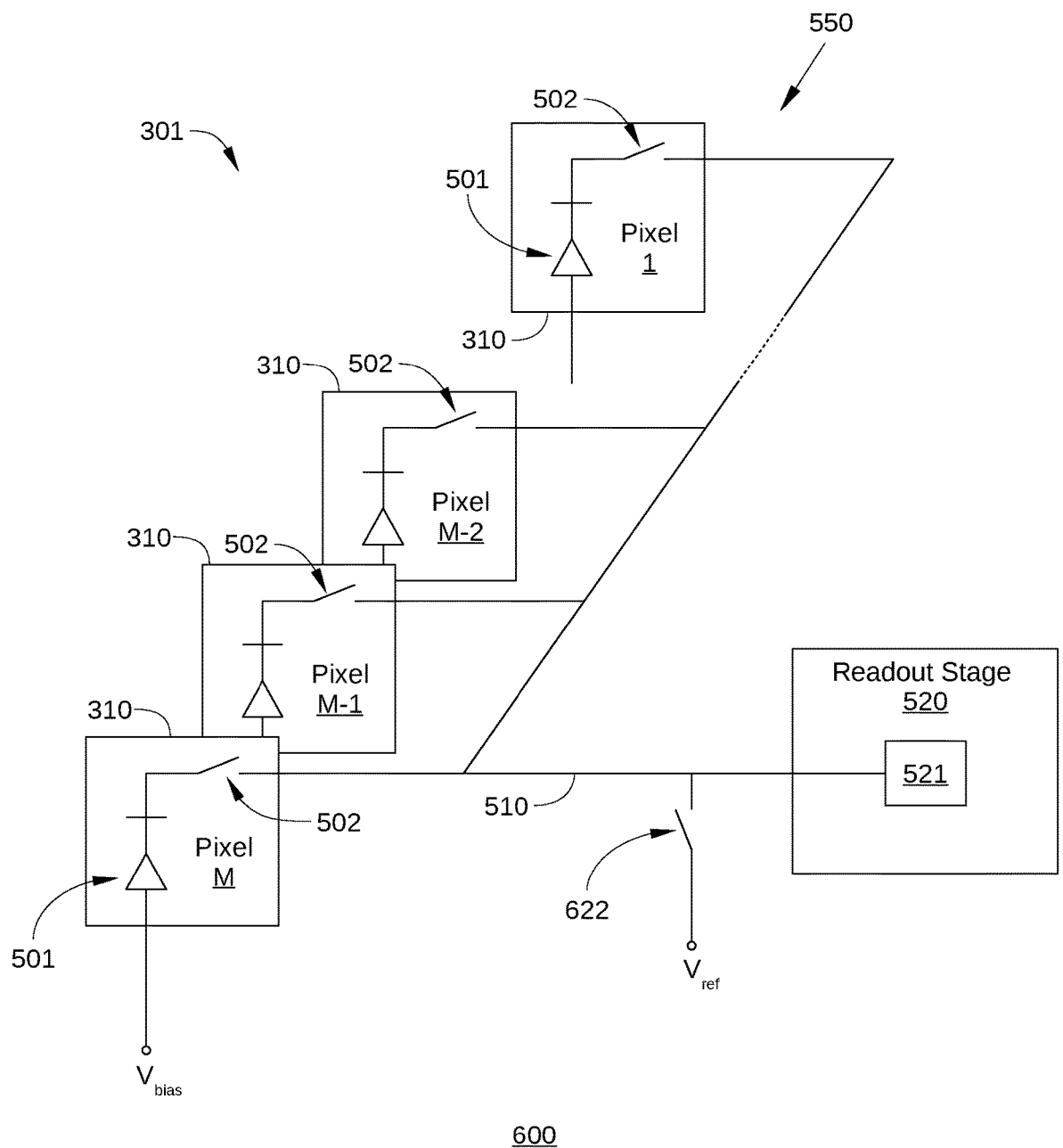
FIG. 6 is a partial circuit diagram of the photosensitive element and detector circuitry layer included in the X-ray imager of FIG. 3, according to another embodiment of the disclosure.
Figure 7:
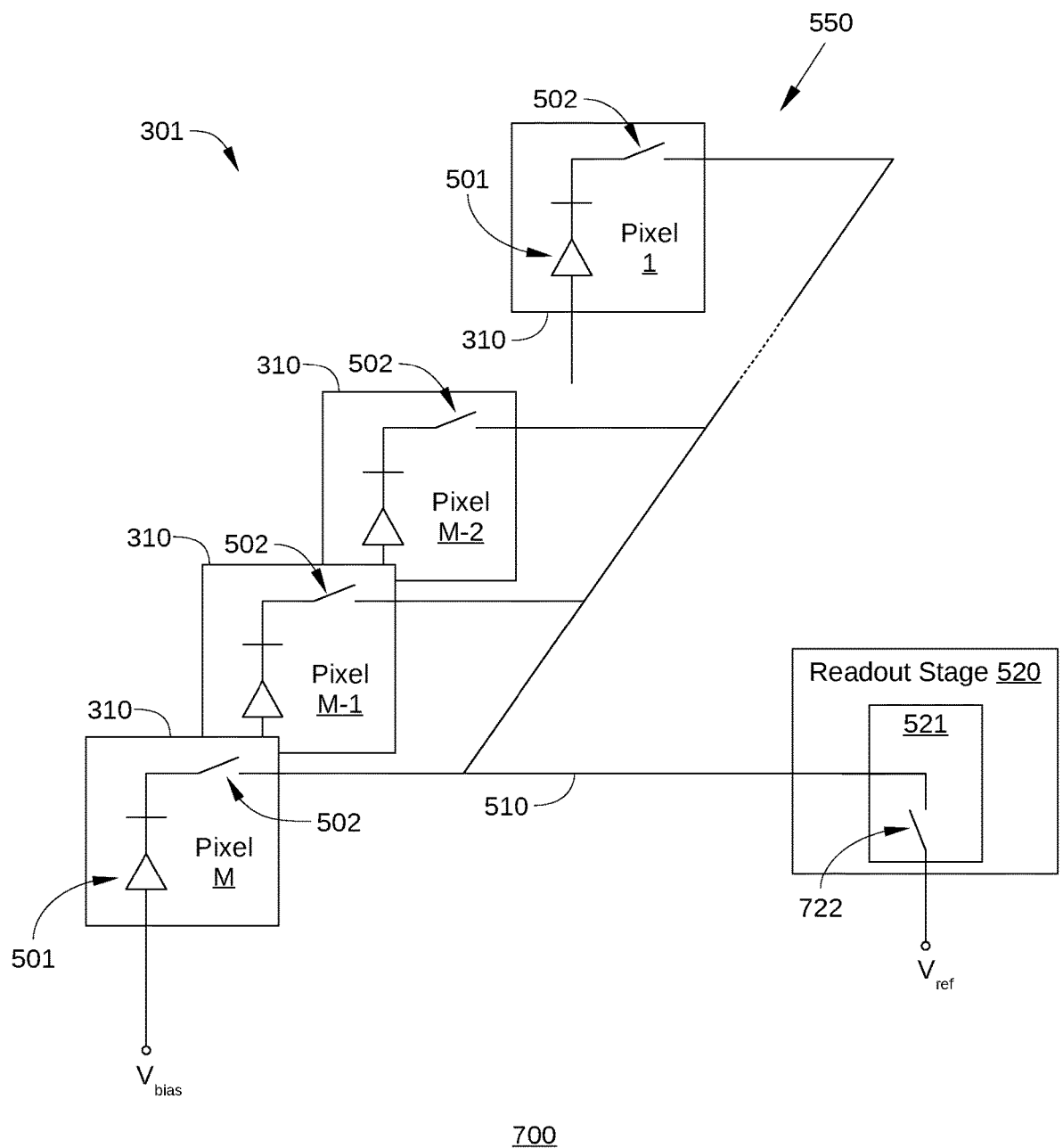
FIG. 7 is a partial circuit diagram of the photosensitive element and detector circuitry layer included in the X-ray imager of FIG. 3, according to yet another embodiment of the disclosure.

In the embodiment illustrated in FIG. 5, reset switch 522 is included in readout stage 520. In other embodiments, a reset switch is still communicatively coupled to data line 510, but is implemented outside of readout stage 520. One such embodiment is illustrated in FIG. 6. FIG. 6 is a partial circuit diagram 600 of photosensitive element and detector circuitry layer 301, according to another embodiment of the disclosure. As shown, in the embodiment illustrated in FIG. 6, a reset switch 622 is configured to selectively couple data line 510 to reference voltage $V_{ref}$, but is located at some other position along data line 510 than readout stage 520. In yet other embodiments, a reset switch is communicatively coupled to data line 510, but is implemented via existing circuitry included in conversion circuitry 521. One such embodiment is illustrated in FIG. 7. FIG. 7 is a partial circuit diagram 700 of photosensitive element and detector circuitry layer 301, according to yet another embodiment of the disclosure. As shown, in the embodiment illustrated in FIG. 7, a reset switch 722 is configured to selectively couple data line 510 to reference voltage $V_{ref}$ and is included within conversion circuitry 521. Alternatively, the functionality of reset switch 722 is implemented by one or more components of conversion circuitry 521, and reset switch 722 is not a dedicated switch or transistor for coupling data line 510 to reference voltage $V_{ref}$.

Reduction of Image Lag Via Pixel Charge Reset

According to various embodiments described herein, the acquisition of an X-ray image with an X-ray imager, such as X-ray imager 207, is performed in three phases: an irradiation phase, a readout phase, and a reset phase. In the irradiation phase, each pixel detector element 310 integrates the charge that is generated through irradiation of the panel with imaging X-rays, via pixel capacitance. In the readout phase, the accumulated charge of each pixel detector element 310 is transferred to readout stage 520 and is processed. In the reset phase, residual charge is transferred from each pixel detector element 310, thereby minimizing or otherwise reducing image lag present in the next X-ray image to be acquired. One such embodiment is described below in conjunction with FIG. 8.

Figure 8:
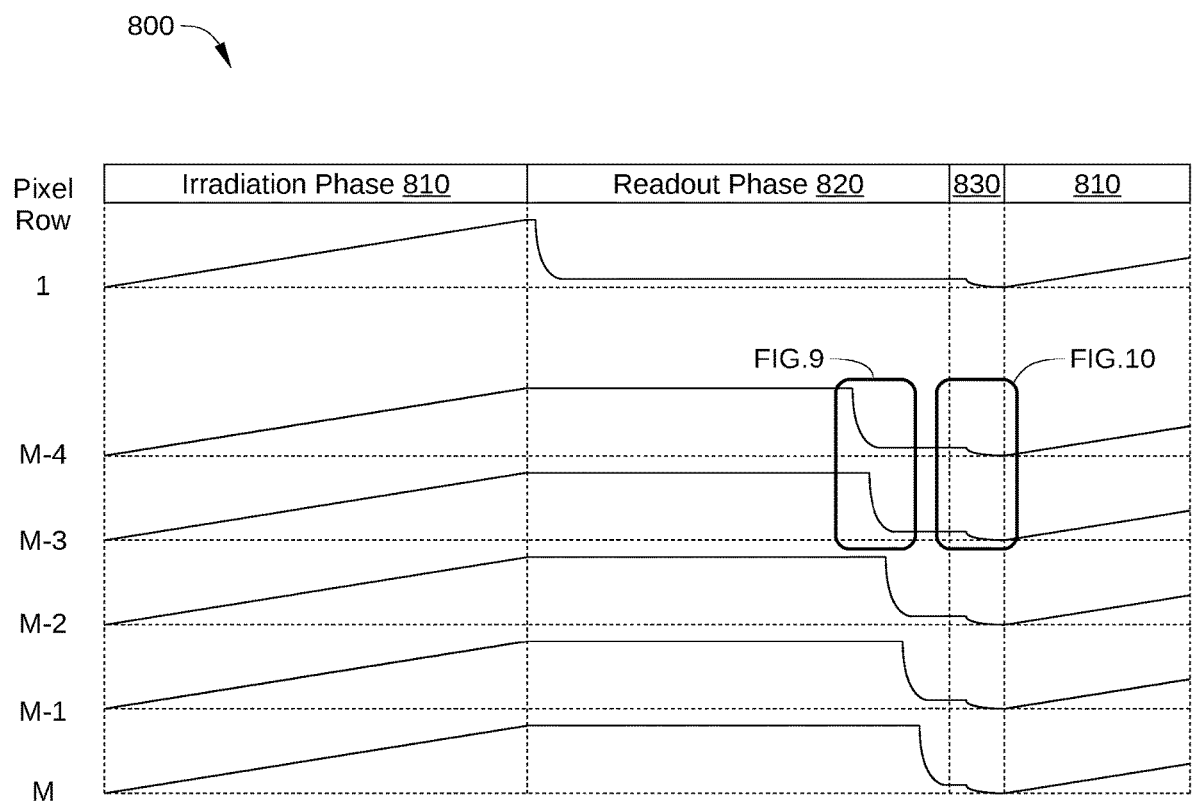
FIG. 8 is a timing diagram schematically illustrating charge accumulation and loss in pixel detector elements during an irradiation phase, a readout phase, and a reset phase of a single X-ray image acquisition, according to an embodiment of the present disclosure.

FIG. 8 is a timing diagram 800 schematically illustrating charge accumulation and loss in pixel detector elements 310 during an irradiation phase 810, a readout phase 820, and a reset phase 830 of a single X-ray image acquisition, according to an embodiment of the present disclosure. More specifically, charge accumulation and loss is shown for M rows of pixel detector elements 310 in an X-ray detector panel that includes an M×N matrix of pixel detector elements 310. One such row is described above in conjunction with FIG. 5.

As shown, throughout irradiation phase 810, each of the M rows are simultaneously irradiated, and charge is accumulated in the pixel detector elements 310 of each row. In readout phase 820, charge accumulated in the pixel detector elements 310 of each row are read out sequentially. That is, the pixel detector elements 310 for row 1 are read out by readout stage 520, then the pixel detector elements 310 for row 2 are read out by readout stage 520, and so on, until the pixel detector elements 310 of all M rows are read out and an X-ray image can be generated. In reset phase 830, residual charge that remains in the pixel detector elements 310 of each row is concurrently transferred from all rows of an X-ray detector panel. Readout phase 820 is described in greater detail below in conjunction with FIG. 9, and reset phase 830 is described in greater detail below in conjunction with FIG. 10.

Figure 9:
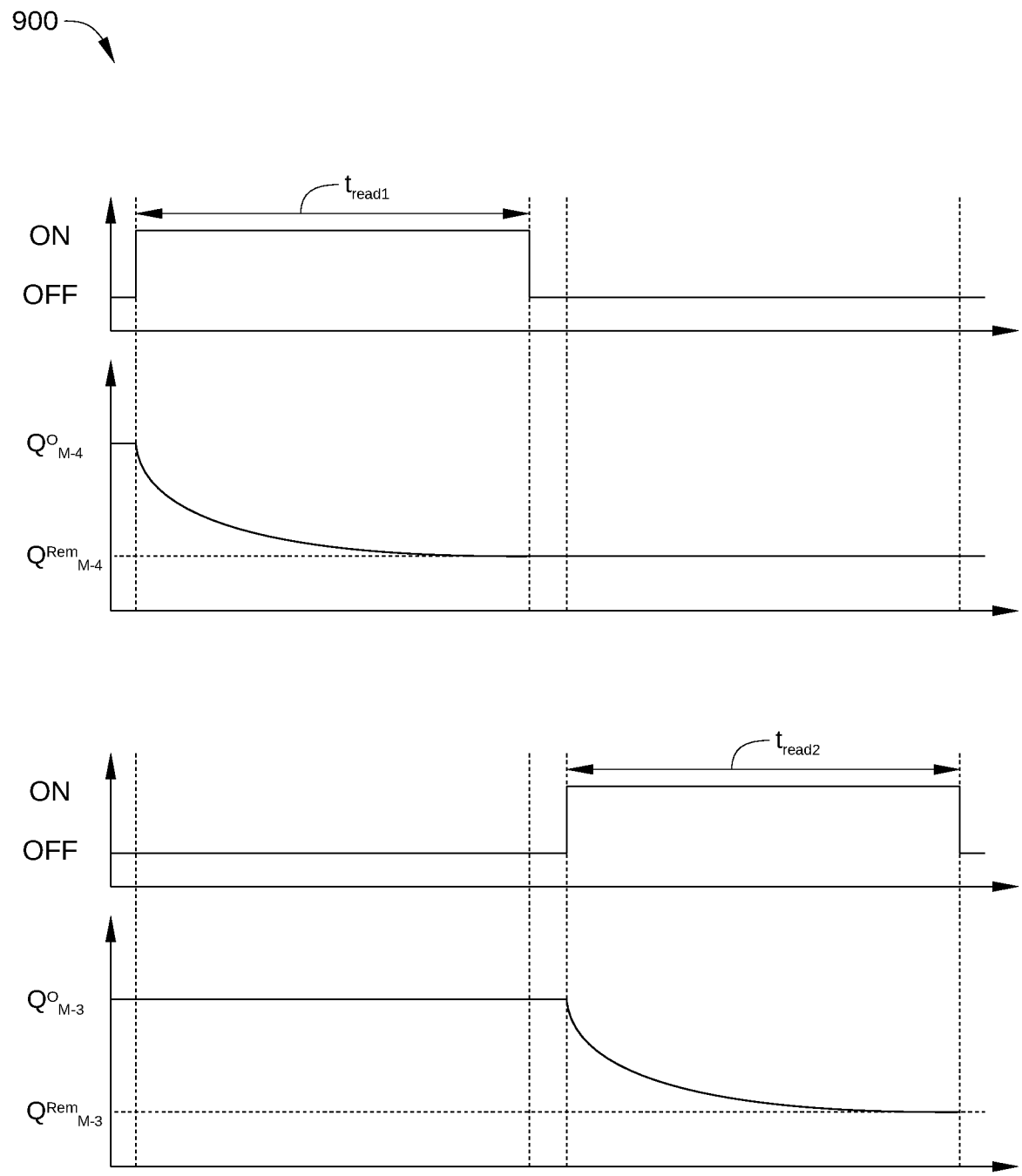
FIG. 9 is a schematic timing diagram illustrating charge loss for two adjacent rows of pixel detector elements during the readout phase of FIG. 8, according to an embodiment of the present disclosure.

FIG. 9 is a schematic timing diagram 900 illustrating charge loss for two adjacent rows of pixel detector elements 310 during readout phase 820, according to an embodiment of the present disclosure. In FIG. 9, a portion of readout phase 820 is shown for a first array (row M-4) of pixel detector elements 310 and an adjacent second array (row M-3) of pixel detector elements 310. During readout phase 820, accumulated charge in each of the pixel detector elements 310 of row M-4 is read during a first readout time interval $t_{read1}$, and accumulated charge in each of the pixel detector elements 310 of row M-3 is read during a second readout time interval $t_{read2}$, that follows first readout time interval $t_{read1}$.

First readout time interval $t_{read1}$ begins after the accumulated charge in each of the pixel detector elements 310 of the preceding row (e.g., row M-5, not shown) has been read out, since photosensitive element and detector circuitry layer 301 is typically connected to a readout stage 520 that is configured to read out one row of pixel detector elements 310 at a time. Similarly, second readout time interval $t_{read2}$ begins after the accumulated charge in each of the pixel detector elements 310 of row M-4 has been read out and first readout time interval tread1 has ended.

During first readout time interval $t_{read1}$, the readout switch 502 for each pixel detector element 310 of row M-4 closes (indicated by ON state in FIG. 9) and an accumulated charge $Q_{M-4}$ decreases in magnitude over first readout time interval $t_{read1}$ from an initial charge value $Q^0_{M-4}$ to a remainder charge value $Q^{Rem}_{M-4}$. The readout switch 502 for each pixel detector element 310 of row M-4 then opens (indicated by OFF state in FIG. 9) and no more charge is read out from the pixel detector element 310 of row M-4. Typically, the value of remainder charge value $Q^{Rem}_{M-4}$ is a function of the duration of first readout time interval $t_{read1}$, a time dependent release of trapped charges, and a pixel time constant $\tau_{pix}$, which is substantially the same for each photodiode 501 of an X-ray imager. For example, in some embodiments, the value of remainder charge value $Q^{Rem}_{M-4}$ can be determined based on Equation 1:

$$Q^{Rem}_{M-4} = Q^O_{M-4} \times \exp(-t_{read1}/T_{pix}) + Q^{trap}_{M-4}(t) \quad (1)$$

Similarly, during second readout time interval $t_{read2}$, the readout switch 502 for each pixel detector element 310 of row M-3 closes (indicated by ON state in FIG. 9) and an accumulated charge $Q_{M-3}$ decreases in magnitude over second readout time interval $t_{read2}$ from an initial charge value Q0M-3 to a remainder charge value $Q^{Rem}_{M-3}$. The readout switch 502 for each pixel detector element 310 of row M-3 then opens (indicated by OFF state in FIG. 9) and no more charge is read out from the pixel detector element 310 of row M-3. This process continues sequentially through the remaining rows of the X-ray imager.

Charge cannot escape from a photodiode 501 once the associated readout switch 502 opens. Therefore, in a conventional X-ray imager, the value of remainder charge value $Q^{Rem}$ for a row corresponds to image lag for each of the pixel detector element 310 of the row, since such remaining charge is present when the subsequent irradiation phase 810 begins. As a result, image quality suffers. Alternatively, the duration of each readout time interval can be increased so that the magnitude of remainder charge value $Q^{Rem}$ is irrelevant. In the latter case, panel readout time of the X-ray imager is greatly slowed, since the panel readout time increases based on the relation: (readout time interval increase)×(number of rows of pixel detector elements). Further, because the rate at which remainder charge value $Q^{Rem}$ decays during readout is an exponential function, a relatively large increase in the readout time interval is required to produce even a small reduction in the remainder charge value $Q^{Rem}$. By contrast, according to various embodiments described herein, reset phase 830 enables remainder charge value $Q^{Rem}$ for each pixel of an X-ray detector panel to be greatly reduced over a relatively short time interval prior to the next irradiation phase 810. Consequently, image lag can be prevented without slowing panel readout time by more than the duration of reset phase 830.

Figure 10:
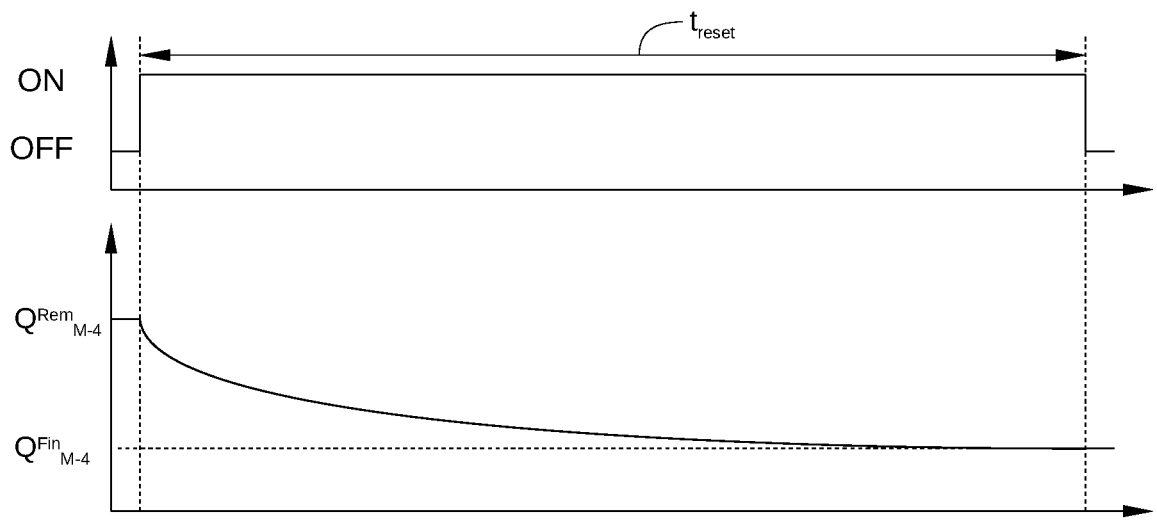
FIG. 10 is a schematic timing diagram illustrating charge loss for two adjacent rows of pixel detector elements during the reset phase of FIG. 8, according to an embodiment of the present disclosure.
Figure 10:
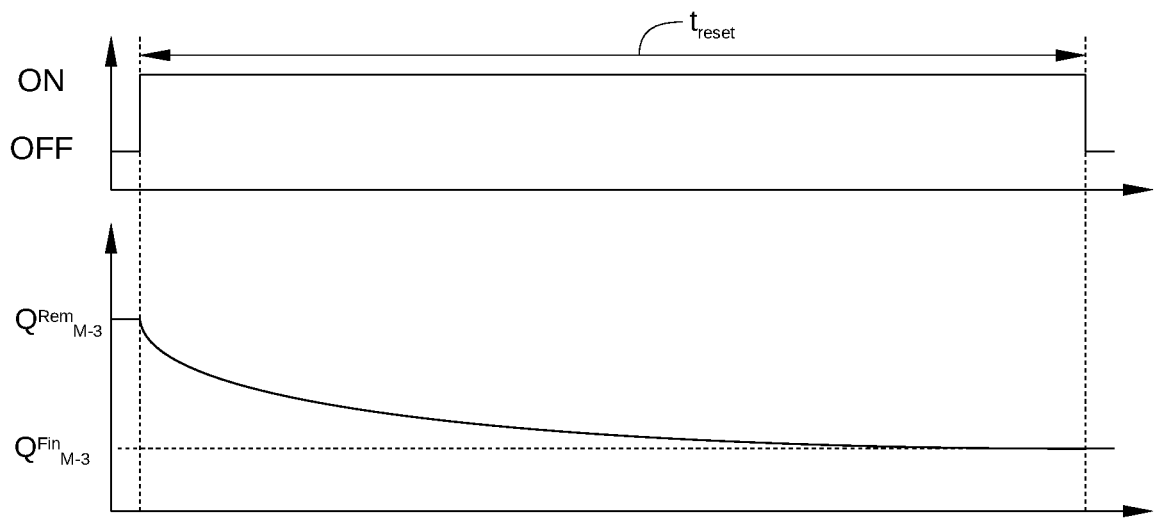

FIG. 10 is a schematic timing diagram 1000 illustrating charge loss for two adjacent rows of pixel detector elements 310 during reset phase 830, according to an embodiment of the present disclosure. In FIG. 10, a portion of reset phase 830 is shown for a first array (row M-4) of pixel detector elements 310 and an adjacent second array (row M-3) of pixel detector elements 310. Reset phase 830 begins after readout phase 820 for all M rows of the X-ray detector panel has been completed.

During reset phase 830, residual charge in each of the pixel detector elements 310 is concurrently transferred from each of the M rows of the X-ray detector panel, for example during a single reset time interval $t_{reset}$. Thus, during reset time interval $t_{reset}$, residual charge in each of the pixel detector elements 310 of row M-4 is transferred from the pixel detector elements, for example to ground or some other suitable reference voltage $V_{ref}$. In addition, during reset time interval $t_{reset}$, residual charge in each of the pixel detector elements 310 of row M-3 is transferred from the pixel detector elements to reference voltage $V_{ref}$. Further, during reset time interval $t_{reset}$, residual charge in each of the pixel detector elements 310 of the remaining rows (not shown) of the X-ray detector panel is transferred from the pixel detector elements to reference voltage $V_{ref}$. Thus, during reset time interval $t_{reset}$, residual charge from some or all of the M rows is concurrently transferred from pixel detector elements 310 to reference voltage $V_{ref}$. As a result, the magnitude of image lag associated with each pixel detector element 310 can be reduced much more quickly than by increasing the duration of the readout time interval $t_{read}$ for each row of pixel detector elements 310.

As shown in FIG. 10, at the beginning of reset time interval $t_{reset}$, residual charge in each particular pixel detector element 310 of row M-4 equals the remainder charge value $Q^{Rem}_{M-4}$, and at the end of reset time interval $t_{reset}$, residual charge in each particular pixel detector element 310 of row M-4 equals a final charge value $Q^{Fin}_{M-4}$ for that particular pixel detector element 310. Similarly, at the beginning of reset time interval $t_{reset}$, residual charge in each particular pixel detector element 310 of row M-3 equals the remainder charge value $Q^{Rem}_{M-3}$ of that particular pixel detector element 310, and at the end of reset time interval $t_{reset}$, residual charge in each particular pixel detector element 310 of row M-3 equals a final charge value $Q^{Fin}_{M-3}$ for that particular pixel detector element 310. Similar to remainder charge value $Q^{Rem}$, in some embodiments, a final charge value $Q^{Fin}$ for each pixel detector element 310 of a particular row (for example row M-3) can be determined based on Equation 2:

$$Q^{Fin}_{M-3} = QO_{M-3} \times \exp(-t_{reset}/\tau pix) + Q^{trap}_{M-4}(t) \quad (2)$$

Thus, the magnitude of $Q^{Fin}$ for pixel detector elements 310 decays at substantially the same rate during reset time interval $t_{reset}$ of reset phase 830 as the magnitude of $Q^{Rem}$ decays during one of the readout time intervals of readout phase 820, such as readout time interval $t_{read1}$. However, in reset phase 830, charge is transferred from some, most, or all of the M rows of the pixel detector elements 310 of the X-ray detector panel simultaneously. Thus, increasing the duration of reset time interval $t_{reset}$ can greatly reduce the magnitude of accumulated charge (from $Q^{Rem}$ to $Q^{Fin}$) in each of the pixel detector elements 310 of an X-ray detector panel without significantly increasing the panel readout time for the X-ray detector panel. By contrast, to achieve the same reduction in accumulated charge (down to $Q^{Fin}$) by increasing the duration of each of the readout time intervals of readout phase 820, the panel readout time for the X-ray detector panel is greatly increased. For example, in one embodiment, reset time interval $t_{reset}$ of reset phase 830 is set to be three times as long as the readout time intervals of readout phase 820. Therefore, panel readout time is increased by 3×(readout time interval $t_{reset}$). To achieve the same reduction in accumulated charge in the pixel detector elements 310 of the X-ray detector panel without using the reset phase 830, the panel readout time is quadrupled, which significantly slows imaging framerate of the X-ray detector.

Figure 11:
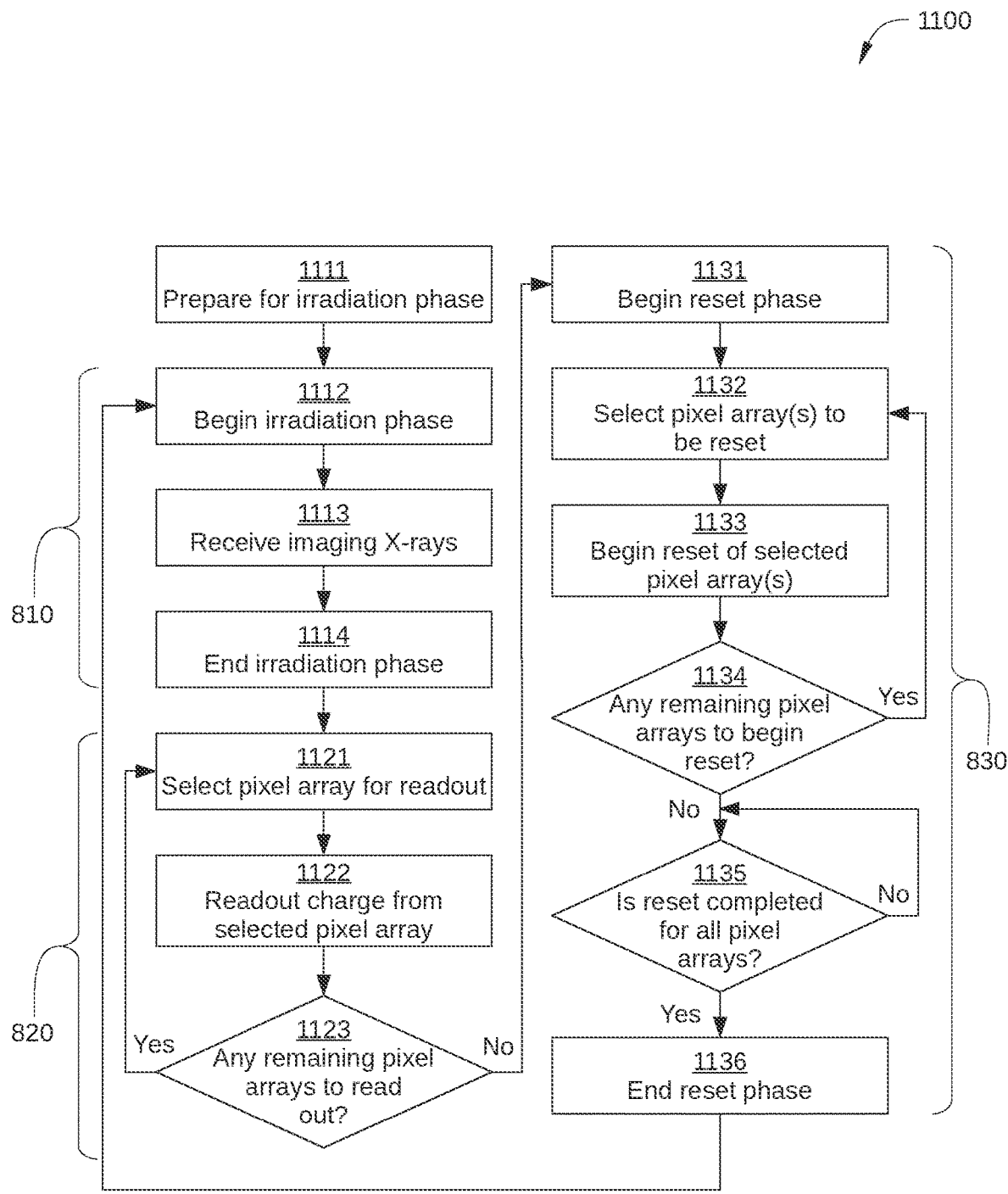
FIG. 11 sets forth a flowchart of a method for acquiring X-ray image data in an X-ray detector panel, according to one or more embodiments of the present disclosure.

FIG. 11 sets forth a flowchart of a method for acquiring X-ray image data in an X-ray detector panel, according to one or more embodiments of the present disclosure. The method may include one or more operations, functions, or actions as illustrated by one or more of blocks 1111-1135. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with the systems of FIGS. 1-10, persons skilled in the art will understand that any suitably configured radiation therapy system is within the scope of the present disclosure. The control algorithms for the method steps can be implemented in whole or in part as software- or firmware-implemented logic, and/or as hardware-implemented logic circuits. Further, the control algorithms for the method steps can be performed in whole or in part by treatment control computer 106 of RT system 100 (shown in FIG. 1), a controller included in X-ray imager 207 (shown in FIG. 2), any other suitable controller associated with RT system 100, or any combination thereof.

A method 1100 begins at step 1111, where treatment control computer 106, a controller included in X-ray imager 207, or any other suitable controller associated with RT system 100 causes X-ray imager 207 to be prepared for irradiation phase 810 and the acquisition of an X-ray image. In some embodiments, the controller causes charge currently accumulated in pixel detector elements 310 of X-ray imager 207 to be transferred to ground or other reference voltage $V_{ref}$. For example, the controller causes readout switch 502 of each pixel detector element 310 and reset switch 522 to close for a certain time interval to reduce accumulated charge in pixel detector elements 310. The controller then causes readout switch 502 of each pixel detector element 310 and reset switch 522 to open.

In step 1112, the controller begins irradiation phase 810. For example, in some embodiments, the controller causes imaging X-ray source 206 to direct imaging X-rays 231 through isocenter 203 of RT system 100 to X-ray imager 207.

In step 1113, X-ray imager 207 receives imaging X-rays 231 and charge is accumulated in some or all of pixel detector elements 310.

In step 1114, the controller ends irradiation phase 810. For example, in some embodiments, the controller causes imaging X-ray source 206 to stop directing imaging X-rays 231 to X-ray imager 207.

In step 1121, the controller selects a pixel array from the M pixel arrays of X-ray imager 207 for readout. In some embodiments, each of the M pixel arrays is configured as a row of pixel detector elements 310. In other embodiments, each of the M pixel arrays is configured as a column of pixel detector elements 310. In yet other embodiments, each of the M pixel arrays is configured as any other group of pixel detector elements 310 that are simultaneously read out by readout stage 520, such as a group of pixel detector elements 310 that are located in a particular region of X-ray imager 207. For clarity, method 1100 is described herein in terms of rows of pixel detector elements 310 included in X-ray imager 207, but method 1100 is equally applicable to any other suitable pixel array configuration of pixel detector elements 310, such as columns or other groups of pixel detector elements 310.

In step 1122, the controller causes accumulated charge from the pixel detector elements 310 of the selected pixel array to be read out during a readout interval. For example, in some embodiments, the controller causes the readout switch 502 of each pixel detector element 310 in the selected pixel array to close for a readout time interval $t_{read}$ while reset switch 522 to reference voltage $V_{ref}$ remains open. As a result, charge currently accumulated in each pixel detector element 310 in the selected pixel array discharges to the readout stage 520, is read by conversion circuitry 521, and is processed as part of the current X-ray image being acquired. During implementation of step 1122, accumulated charge present in each pixel detector element 310 in the selected pixel array is reduced from an initial charge value $Q^0$ to a remainder charge value $Q^{Rem}$ at a rate described by previously presented Equation 1. It is noted that initial charge value $Q^0$ is generally different for each pixel detector element 310. Similarly, remainder charge value $Q^{Rem}$ is a function of initial charge value $Q^0$ and therefore is also generally different for each pixel detector element 310.

In step 1123, the controller determines whether there are remaining pixel arrays to be read out. If yes, method 1100 returns to step 1121; if no, method 1100 proceeds to step 1131.

In step 1131, the controller begins reset phase 830. For example, in some embodiments, the controller causes reset switch 522 to close, and data line 510 is communicatively coupled to $V_{ref}$.

In step 1132, the controller selects one or more pixel arrays of X-ray detector 207 to be reset. For example, in the embodiment of reset phase 830 illustrated in FIG. 10, the controller selects multiple pixel arrays of X-ray detector 207, i.e., all M rows of pixel detector elements 310. In such embodiments, remainder charge value $Q^{Rem}$ for the pixel detector elements 310 of all M rows is reduced simultaneously. Alternatively, in some embodiments, a staged reset of pixel arrays is performed in a reset phase. In such embodiments, the peak current that is exposed to readout stage 522 during reset phase 830 can be reduced by preventing all pixel arrays of X-ray detector 207 from simultaneously being coupled to data line 510. Thus, in some embodiments, in step 1132, the controller selects a portion of the total M rows of pixel arrays to begin being reset in step 1133, for example one tenth of the M rows. In such embodiments, subsequent portions are selected to begin being reset while the previously selected portions continue to be reset. One such embodiment is illustrated in FIGS. 12A and 12B.

Figure 12A:
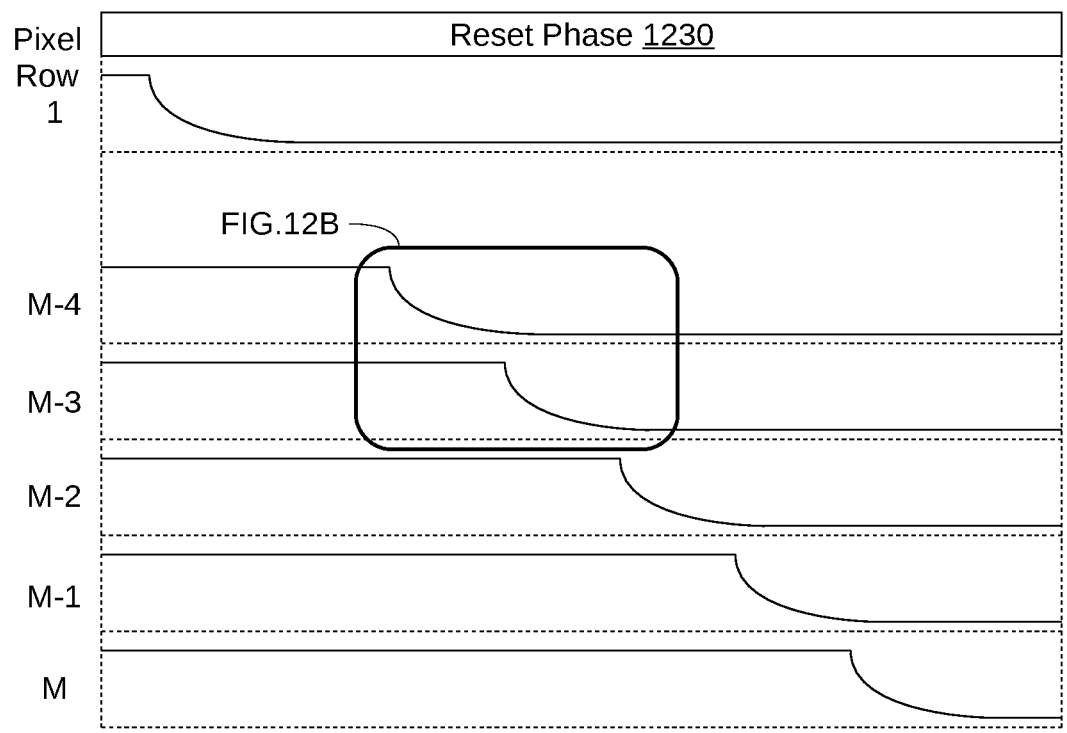
FIG. 12A is a timing diagram schematically illustrating charge loss for different rows of pixel detector elements during a reset phase, according to an embodiment of the present disclosure.

FIG. 12A is a timing diagram 1200 schematically illustrating charge loss for different rows of pixel detector elements 310 during reset phase 1230, according to an embodiment of the present disclosure. FIG. 12B illustrates a portion of reset phase 1230 for a first array (row M-4) of pixel detector elements 310 and an adjacent second array (row M-3) of pixel detector elements 310, according to an embodiment of the present disclosure.

Reset phase 1230 is similar to reset phase 830 of FIG. 8, in that during reset phase 1230, residual charge in each pixel detector element 310 of multiple rows of an X-ray detector panel is transferred from the pixel detector elements concurrently. That is, during at least a portion of reset phase 1230, multiple rows of an X-ray detector panel are undergoing reset simultaneously and accumulated charge is being transferred simultaneously from all pixel detector elements 310 associated with the multiple rows. However, in reset phase 1230, the reset time interval $t_{reset}$ begins at different times for different rows of pixel detector elements 310. Thus, reset of the M rows of pixel detector elements 310 is staged throughout reset phase 1230. Consequently, the larger initial current in data line 510 that results when a row of pixel detector elements 310 is initially coupled thereto does not occur for all rows of pixel detector elements 310 simultaneously. Instead, the rows of pixel detector elements 310 are initially coupled to data line 510 and readout stage 522 at different times in reset phase 1230.

Figure 12B:
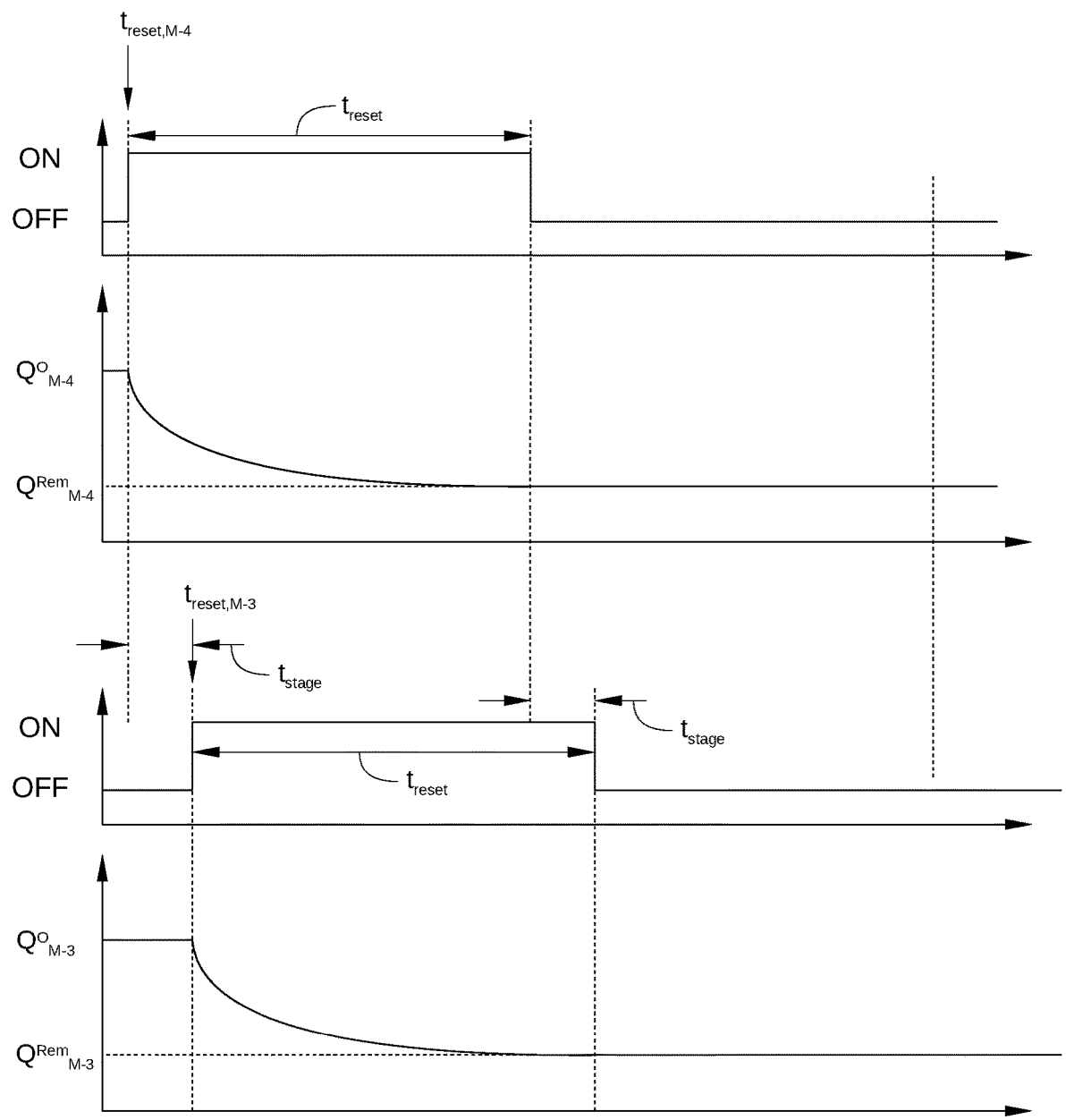
FIG. 12B illustrates a portion of the reset phase of FIG. 12A for a first array of pixel detector elements and an adjacent second array of pixel detector elements, according to an embodiment of the present disclosure.

In the embodiment illustrated in FIGS. 12A and 12B, each of the M rows of pixel detector elements 310 is initially coupled to readout stage 522 at a different time in reset phase 1230. Thus, in such an embodiment, each row of pixel detector elements 310 is associated with a different reset initiating time. For example, as shown in FIG. 12B, reset of the pixel detector elements 310 of row M-4 is initiated at a reset initiating time $t_{reset}/M$-4, while reset of the pixel detector elements 310 of row M-3 is initiated at a reset initiating time $t_{reset}$,M-3. In some embodiments, $t_{reset,M-3}$ is separated in time from reset initiating time $t_{reset}$,M-4 by a staging time interval $t_{stage}$. In some embodiments, staging time interval $t_{stage}$ is generally uniform between consecutive rows of pixel detector elements 310, while in other embodiments, staging time interval $t_{stage}$ can vary between different consecutive rows of pixel detector elements 310. Generally, the duration of staging time interval $t_{stage}$ is relatively small compared to the duration of reset phase 1230. Consequently, in embodiments in which the reset of the M rows of pixel detector elements 310 is staged throughout reset phase 1230, the overall duration of reset phase 1230 is not significantly increased.

In the embodiment illustrated in FIGS. 12A and 12B, each of the M rows of pixel detector elements 310 is initially coupled to readout stage 522 at a unique time in reset phase 1230. Alternatively, in some embodiments, a first group of multiple rows of pixel detector elements 310 are initially coupled to readout stage 522 at one time in reset phase 1230, a second group of multiple rows of pixel detector elements 310 are initially coupled to readout stage 522 at a later time in reset phase 1230, a third group of multiple rows of pixel detector elements 310 are initially coupled to readout stage 522 at another later time in reset phase 1230, and so on. For example, in one such embodiment, each such group of multiple rows of pixel detector elements 310 includes 10% of the M rows of pixel detector elements 310 and each such group includes different rows of pixel detector elements 310 than the other rows of pixel detector elements. Thus, in such an embodiment, reset phase 1230 includes 10 different reset initiating times, rather than one reset initiating time for each row of pixel detector elements.

Returning to FIG. 11, in step 1133, the controller causes the row or rows of pixel detector elements 310 selected in step 1132 to be reset. For example, in some embodiments, the controller causes reset switch 522 to close, thereby communicatively coupling data line 510 to reference voltage $V_{ref}$. Furthermore, the controller causes the readout switch 502 of each pixel detector element 310 in the selected row or rows to close, thereby communicatively coupling such pixel detector elements 310 to data line 510. As a result, charge present in the pixel detector elements 310 (e.g., remainder charge value $Q^{Rem}$) begins to be transferred to reference voltage $V_{ref}$. Thus, the charge present in the pixel detector elements 310 is reduced at a rate indicated by previously presented Equation 2.

In embodiments in which all M rows of pixel detector elements 310 are selected in step 1131, all pixel detector elements 310 of X-ray imager 207 are reset simultaneously. In such embodiments, after reset time interval $t_{reset}$ has elapsed, method 1100 proceeds to step 1133.

In embodiments in which a staged reset of pixel arrays is performed in the reset phase, a single row of pixel detector elements 310 begins to be reset in step 1132 or a group of rows of pixel detector elements 310 begins to be reset in step 1132. In such embodiments, after a staging time interval $t_{stage}$ has elapsed, method 1100 proceeds to step 1133.

In step 1134, the controller determines whether there are remaining pixel arrays that have not yet begun being reset. If yes, method returns to step 1132; if no, method 1100 proceeds to step 1135. It is noted that in embodiments in which a staged reset of pixel arrays is performed in the reset phase, method 1100 may return to step 1132 while some pixel arrays of X-ray imager 207 are currently being reset. That is, the controller may perform step 1134 before reset time interval $t_{reset}$ has elapsed for some or all pixel arrays that have been selected to be reset.

In step 1135, the controller determines whether reset has been completed for all pixel arrays. That is, the controller determines whether reset time interval $t_{reset}$ has elapsed for all pixel arrays of X-ray imager 207. If no, method 1100 returns back to step 1135; if yes, method 1100 proceeds to step 1136.

In step 1136, the controller ends the reset phase. For example, in some embodiments, the controller causes reset switch 522 to open and the readout switch 502 of each pixel detector element 310 of X-ray imager 207 to open. When acquisition of further X-ray images is planned, method 1100 returns back to step 1112.

Implementation of method 1100 enables a significant reduction in charge remaining in pixel detector elements 310 (for example from $Q^{Rem}$ to $Q^{Fin}$) over a reset time interval $t_{reset}$. As noted above, reset time interval $t_{reset}$ can be selected to be relatively short compared to the duration of a readout time interval. In a conventional X-ray imager, an equivalent charge reduction can only be realized over a much greater time interval, i.e., (reset time interval $t_{reset}$)×(number of rows of pixel detector elements 310). Since the number of rows of pixel detector elements 310 can be on the order of 1000 to 4000, the panel readout time for the conventional X-ray imager can be significantly increased, preventing fast image acquisition.

Synchronizing Reset with Application of Treatment Beam

In practice, a treatment beam in an RT system typically generates a large amount of scattered radiation in all directions, including that emanating from the patient, treatment table, and machine components. As a result, a large amount of MV scatter can be incident on an X-ray imager (e.g., X-ray imager 207 in FIG. 2). In some instances, the amount of such X-ray scatter can even exceed the magnitude of imaging X-rays. Accordingly, in some embodiments, a reset phase, such as reset phase 830 or reset phase 1230, is timed to coincide with the application of a treatment beam, such as treatment beam 230. X-ray imager 207 is insensitive to radiation during a reset phase as described herein. That is, pixel detector elements 310 of X-ray imager 207 do not accumulate charge during such a reset phase, even when treatment beam 230 produces significant X-ray scatter that is incident on X-ray imager 207. As a result, the implementation of the reset phase to coincide with a burst or other application of treatment beam 231 reduces noise that is normally induced by treatment beam 230. One such embodiment is illustrated in FIG. 13.

Figure 13:
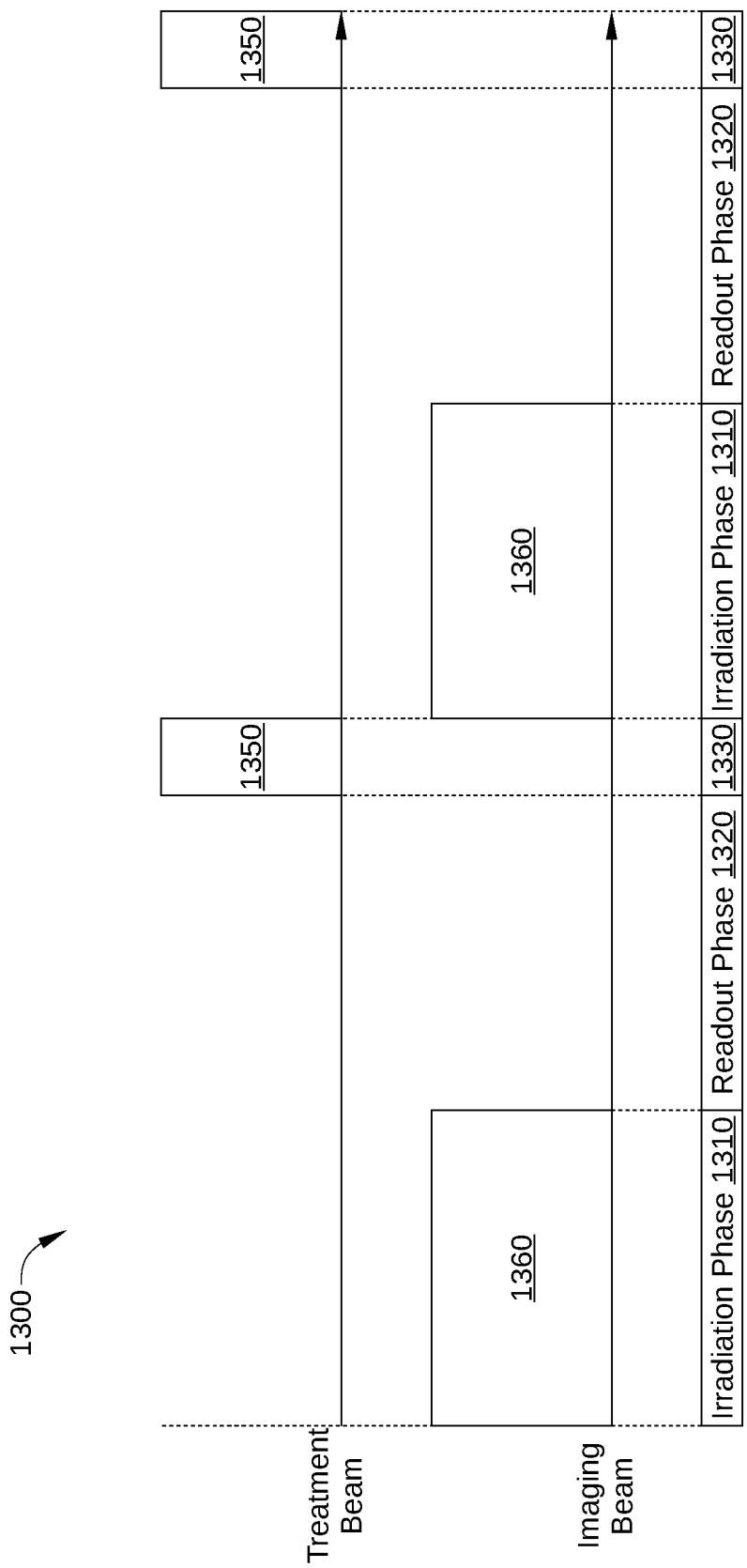
FIG. 13 is a timing diagram schematically illustrating the relative timing of an irradiation phase, a readout phase, and a reset phase relative to the delivery of a treatment beam pulse 1350, according to an embodiment of the present disclosure.

FIG. 13 is a timing diagram 1300 schematically illustrating the relative timing of an irradiation phase 1310, a readout phase 1320, and a reset phase 1330 relative to the delivery of a treatment beam pulse 1350, according to an embodiment of the present disclosure. As shown, a KV (imaging) beam pulse 1360 occurs during each irradiation phase 1310 and delivery of treatment beam pulse 1350 is timed to occur during each reset phase 1330. As described above, pixel detector elements 310 of X-ray imager 207 do not accumulate charge during a reset phase. Consequently, even though scattered X-rays from treatment beam pulses 1350 may strike the scintillator layer of X-ray imager 207, noise is not added to the image data generated by X-ray imager 207.

While the embodiments are described herein with respect to an X-ray imager included in an RT system, the embodiments are equally applicable to other X-ray imaging systems. For example, the embodiments can also be implemented in a hand-held or portable flat panel X-ray detector (FPD), a statically mounted FPD, an X-ray imager configured for dynamic X-ray imaging, such as a fluoroscopic imaging, and the like. Further, the embodiments can be employed for the detection in intra-fraction motion or pre-treatment imaging prior to treatment.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A method of acquiring an X-ray image of a target volume, the method comprising:
    transferring accumulated charge from each pixel in a first array of pixels of an X-ray detector panel to a readout device during a first readout interval, wherein residual charge remains in each pixel in the first array of pixels after the transferring;
    after the first readout interval, transferring accumulated charge from each pixel in a second array of pixels of the X-ray detector panel to the readout device during a second readout interval, wherein residual charge remains in each pixel in the second array of pixels after the transferring of accumulated charge from each pixel in the second array of pixels; and
    during a reset interval that follows the second readout interval, concurrently transferring at least a portion of the residual charge from each pixel in the first array of pixels and at least a portion of the residual charge from each pixel in the second array of pixels,
    wherein transferring residual charge from each pixel in the first array of pixels comprises electrically coupling each pixel in the first array of pixels to a reference voltage associated with the readout device and transferring residual charge from each pixel in the second array of pixels comprises electrically coupling each pixel in the second array of pixels to the reference voltage associated with the readout device.

2. The method of claim 1, further comprising, during the reset interval, concurrently transferring at least a portion of the residual charge from each pixel in each array of pixels of the X-ray detector panel to the reference voltage associated with the readout device.

3. The method of claim 1, wherein electrically coupling each pixel in the first array of pixels to the reference voltage associated with the readout device comprises electrically coupling each pixel in the first array of pixels to the readout device.

4. The method of claim 1, wherein the first array of pixels comprises a first row of pixels and the second array of pixels comprises a second row of pixels.

5. The method of claim 1, wherein a start time of the reset interval is selected to occur prior to a treatment beam pulse and an end time of the reset interval is selected to occur after the treatment beam pulse.

6. The method of claim 5, wherein a megavolt treatment beam is directed to the target volume during the treatment beam pulse.

7. The method of claim 1, wherein concurrently transferring at least the portion of the residual charge from each pixel in the first array of pixels and at least the portion of the residual charge from each pixel in the second array of pixels comprises:
    communicatively coupling the first array of pixels to the reference voltage so that the residual charge from each pixel in the first array of pixels begins to be transferred to the reference voltage; and
    while the residual charge from each pixel in the first array of pixels is being transferred to the reference voltage, communicatively coupling the second array of pixels to the reference voltage so that the residual charge from each pixel in the second array of pixels begins to be transferred to the reference voltage.

8. The method of claim 1, wherein concurrently transferring at least the portion of the residual charge from each pixel in the first array of pixels and at least the portion of the residual charge from each pixel in the second array of pixels comprises:
    communicatively coupling a first group of arrays of pixels that includes the first array of pixels to the reference voltage so that the residual charge from each pixel in the first group of arrays of pixels begins to be transferred to the reference voltage; and
    while the residual charge from each pixel in the first group of arrays of pixels is being transferred to the reference voltage, communicatively coupling a second group of arrays of pixels that includes the second array of pixels to the reference voltage so that the residual charge from each pixel in the second group of arrays of pixels begins to be transferred to the reference voltage.

9. The method of claim 1, further comprising:
    prior to the first readout interval, preparing each pixel in the first array of pixels and each pixel in the second array of pixels to accumulate charge in response to incident X-rays; and causing imaging X-rays to be directed to the X-ray detector panel.

10. An apparatus comprising:
an imaging X-ray source configured to direct imaging X-rays through a target volume and toward an X-ray detector panel; and
a controller configured to:
cause accumulated charge from each pixel in a first array of pixels of the X-ray detector panel to be transferred to a readout device during a first readout interval, wherein residual charge remains in each pixel in the first array of pixels after the transferring;
after the first readout interval, causing accumulated charge from each pixel in a second array of pixels of the X-ray detector panel to be transferred to the readout device during a second readout interval, wherein residual charge remains in each pixel in the second array of pixels after the transferring of accumulated charge from each pixel in the second array of pixels; and
during a reset interval that follows the second readout interval, causing at least a portion of the residual charge to be transferred from each pixel in the first array of pixels and concurrently causing at least a portion of the residual charge to be transferred from each pixel in the second array of pixels,
wherein transferring residual charge from each pixel in the first array of pixels comprises electrically coupling each pixel in the first array of pixels to a reference voltage associated with the readout device and transferring residual charge from each pixel in the second array of pixels comprises electrically coupling each pixel in the second array of pixels to the reference voltage associated with the readout device.

11. The apparatus of claim 10, wherein the controller is further configured to, during the reset interval, concurrently transfer at least a portion of the residual charge from each pixel in each array of pixels of the X-ray detector panel to the reference voltage associated with the readout device.

12. The apparatus of claim 10, wherein electrically coupling each pixel in the first array of pixels to the reference voltage associated with the readout device comprises electrically coupling each pixel in the first array of pixels to the readout device.

13. The apparatus of claim 10, wherein the first array of pixels comprises a first row of pixels and the second array of pixels comprises a second row of pixels.

14. The apparatus of claim 10, wherein a start time of the reset interval is selected to occur prior to a treatment beam pulse and an end time of the reset interval is selected to occur after the treatment beam pulse.

15. The apparatus of claim 10, wherein concurrently transferring at least the portion of the residual charge from each pixel in the first array of pixels and at least the portion of the residual charge from each pixel in the second array of pixels comprises:
communicatively coupling the first array of pixels to the reference voltage so that the residual charge from each pixel in the first array of pixels begins to be transferred to the reference voltage; and
while the residual charge from each pixel in the first array of pixels is being transferred to the reference voltage, communicatively coupling the second array of pixels to the reference voltage so that the residual charge from each pixel in the second array of pixels begins to be transferred to the reference voltage.

16. The apparatus of claim 10, wherein concurrently transferring at least the portion of the residual charge from each pixel in the first array of pixels and at least the portion of the residual charge from each pixel in the second array of pixels comprises:
communicatively coupling a first group of arrays of pixels that includes the first array of pixels to the reference voltage so that the residual charge from each pixel in the first group of arrays of pixels begins to be transferred to the reference voltage; and
while the residual charge from each pixel in the first group of arrays of pixels is being transferred to the reference voltage, communicatively coupling a second group of arrays of pixels that includes the second array of pixels to the reference voltage so that the residual charge from each pixel in the second group of arrays of pixels begins to be transferred to the reference voltage.

17. An apparatus comprising:
an imaging X-ray source configured to direct imaging X-rays through a target volume and toward an X-ray detector panel; and
a controller configured to:
cause accumulated charge from each pixel in a first array of pixels of the X-ray detector panel to be transferred to a readout device during a first readout interval, wherein residual charge remains in each pixel in the first array of pixels after the transferring;
after the first readout interval, causing accumulated charge from each pixel in a second array of pixels of the X-ray detector panel to be transferred to the readout device during a second readout interval, wherein residual charge remains in each pixel in the second array of pixels after the transferring of accumulated charge from each pixel in the second array of pixels; and
during a reset interval that follows the second readout interval, causing at least a portion of the residual charge to be transferred from each pixel in the first array of pixels and concurrently causing at least a portion of the residual charge to be transferred from each pixel in the second array of pixels,
wherein a start time of the reset interval is selected to occur prior to a treatment beam pulse and an end time of the reset interval is selected to occur after the treatment beam pulse.

18. The system of claim 17, wherein a megavolt treatment beam is directed to the target volume during the treatment beam pulse.

19. The apparatus of claim 17, wherein transferring residual charge from each pixel in the first array of pixels to the readout device comprises electrically coupling the first array of pixels to a readout stage of the readout device.

20. The apparatus of claim 17, wherein transferring residual charge from each pixel in the first array of pixels comprises electrically coupling each pixel in the first array of pixels to a reference voltage.

* * * * *